United States Patent [19]

Bell et al.

[11] Patent Number: 5,709,934
[45] Date of Patent: Jan. 20, 1998

[54] BIPOLYMER FOAMS HAVING EXTRACELLULAR MATRIX PARTICULATES

[75] Inventors: Eugene Bell, Boston; Timothy W. Fofonoff, Dedham, both of Mass.

[73] Assignee: Tissue Engineering, Inc., Boston, Mass.

[21] Appl. No.: 343,172

[22] Filed: Nov. 22, 1994

[51] Int. Cl.$^6$ .................................. A61L 27/00; B32B 3/00
[52] U.S. Cl. .................. 428/305.5; 428/323; 424/423; 424/425; 424/426; 623/1; 623/12; 623/15
[58] Field of Search ..................... 408/305.5, 323, 408/304.4; 424/423, 426, 425; 623/1, 12, 15

[56] References Cited

U.S. PATENT DOCUMENTS

| | | | |
|---|---|---|---|
| 3,800,792 | 4/1974 | McKnight et al. | 128/156 |
| 4,148,664 | 4/1979 | Cruz, Jr. | 106/161 |
| 4,294,241 | 10/1981 | Miyata | 126/156 |
| 4,472,840 | 9/1984 | Jefferies | 3/1.9 |
| 4,485,096 | 11/1984 | Bell | 424/95 |
| 4,485,097 | 11/1984 | Bell | 424/95 |
| 4,501,815 | 2/1985 | Reid et al. | 435/284 |
| 4,505,266 | 3/1985 | Yannas et al. | 128/1 R |
| 4,642,292 | 2/1987 | Reid et al. | 435/240 |
| 4,645,669 | 2/1987 | Reid | 424/95 |
| 4,661,111 | 4/1987 | Ruoslahti et al. | 623/11 |
| 4,776,853 | 10/1988 | Klement et al. | 8/94.11 |
| 4,795,459 | 1/1989 | Jauregui | 623/1 |
| 4,801,299 | 1/1989 | Brendel et al. | 623/1 |
| 4,835,803 | 6/1989 | Mizushima | 8/128.1 |
| 4,837,285 | 6/1989 | Berg et al. | 530/356 |
| 4,891,359 | 1/1990 | Saferstein et al. | 514/21 |
| 4,902,508 | 2/1990 | Badylak et al. | 424/95 |
| 4,925,924 | 5/1990 | Silver et al. | 530/356 |
| 4,935,000 | 6/1990 | Dudek | 600/36 |
| 4,950,483 | 8/1990 | Ksander et al. | 424/422 |
| 4,956,178 | 9/1990 | Badylak et al. | 424/551 |
| 4,969,912 | 11/1990 | Kelman et al. | 623/66 |
| 4,981,841 | 1/1991 | Gibson | 514/4 |
| 4,983,580 | 1/1991 | Gibson | 514/2 |
| 5,007,916 | 4/1991 | Linsky et al. | 606/151 |
| 5,024,841 | 6/1991 | Chu et al. | 424/422 |
| 5,043,278 | 8/1991 | Nagaoka et al. | 435/181 |
| 5,043,426 | 8/1991 | Goldstein | 530/356 |
| 5,110,604 | 5/1992 | Chu et al. | 424/484 |
| 5,116,552 | 5/1992 | Morita et al. | 264/28 |
| 5,171,273 | 12/1992 | Silver et al. | 623/13 |
| 5,192,312 | 3/1993 | Orton | 623/2 |
| 5,254,471 | 10/1993 | Mori et al. | 435/240.23 |
| 5,399,361 | 3/1995 | Song et al. | 424/486 |

FOREIGN PATENT DOCUMENTS

| | | |
|---|---|---|
| 0 358 506 A3 | 3/1990 | European Pat. Off. . |
| 0 531 733 | 3/1993 | European Pat. Off. . |
| 0 562 864 | 9/1993 | European Pat. Off. . |
| 0 568 334 | 11/1993 | European Pat. Off. . |
| 1158963 | 6/1989 | Japan . |
| WO 85/04413 | 10/1985 | WIPO . |
| WO 94/03584 | 2/1994 | WIPO . |
| WO 95/26168 | 10/1995 | WIPO . |
| 96/05818 | 5/1996 | WIPO . |

OTHER PUBLICATIONS

Adams, J.C. and Watt, F.M., "Regulation of Development and Differentiation by the Extracellular Matrix," *Development*, 117:1183–1198 (1993).

Edgington, Stephen M., "3–D Biotech: Tissue Engineering," *Bio/Tehnology*, 10:855–860 (Aug. 1992).

Lin, C.Q. and Bissell, M.J., "Multi-faceted Regulation of Cell Differentiation by Extracellular Matrix," *The FASEB Journal*, 7(737–743 (Jun. 1993).

Nathan, C.and Sporn, M., "Cytokines in Context," *The Journal of Cell Biology*, 113:981–986 (1991).

Woessner, J. Frederick, Jr., "Introduction to Serial Reviews: The Extracellular Matrix," *The FASEB Journal*, 7:735–736 (Jun. 1993).

DeBlois, C., et al., "Heparin–Fibroblast Growth Factor–Fibrin Complex: In Vitro and in Vivo Applications to Collagen–Based Materials," *Baterials*, vol. 15, No. 9, 665–672 (1994).

Mizuno, S., et al., "A Collagen/DBP Sponge System Designed for in Vitro Analysis of Chondroinduction," *Materials Research Society Symposium Proceedings*, vol. 252, 133–141 (1992).

*Primary Examiner*—Kathleen Choi
*Attorney, Agent, or Firm*—Lahive & Cockfield, LLP

[57] ABSTRACT

A biopolymer solution is polymerized to form a gel which is freeze-dried and crosslinked with ultraviolet radiation to form a biopolymer foam. The foam is filled with a collagen solution and the combination is freeze-dried or the foam is filled with a collagen solution containing extracellular matrix particulates and that combination is freeze-dried, thereby forming a foam to which extracellular matrix particulates are attached.

23 Claims, No Drawings

BIPOLYMER FOAMS HAVING EXTRACELLULAR MATRIX PARTICULATES

BACKGROUND OF THE INVENTION

Collagen sponges or foams have been used as hemostatic agents and more recently as scaffolds for tissue repair in vivo and as research tools in vivo for seeding various cell types to study cell functions in three dimensions. Collagen sponges have a low immunogenicity and consist of a naturally occurring structural protein to which cells can attach, interact with and degrade. In vivo they are bioabsorbable. However, sponges are usually crosslinked to provide the degree of wet strength and measured resistance to dissolution needed for many of the above-referenced uses. In general, crosslinking reduces or degrades the normal binding sites seen by other molecules and cells in cell and tissue interactions with the extracellular matrix that surrounds cells. Further, collagen sponges, gelatin sponges or polyvinyl alcohol sponges lack biological activity typically present in the extracellular matrix environment of cells. However, because of their deficiencies, crosslinked collagen sponges induce little regeneration in vitro or serve poorly as histiotypic and organotypic models in vitro.

A need exist, therefore, for an improved biopolymer foam that overcomes or minimizes the above-mentioned problems.

SUMMARY OF THE INVENTION

The invention includes a sponge and method for forming a foam having extracellular matrix particulates.

The sponge is formed with a biopolymer foam and extracellular matrix particulates. The method includes forming a biopolymer solution and polymerizing the biopolymer in the biopolymer solution, thereby forming a biopolymer lattice. The biopolymer lattice is crosslinked to form a foam, which is freeze-dried. Extracellular matrix particulates suspended in a solution of collagen are applied to the freeze-dried foam, thereby forming the foam having extracellular matrix particulates.

The present invention has many advantages. One advantage is that a three-dimensional model system can be formed, which has many uses. These uses include a device for conducting basic or applied research, a device which can be seeded with abnormal cells to study disease states including cancer, a device which can serve as a diagnostic test for determining chemotherapeutic strategies by selecting for agents capable of killing cancer cells cultivated in or on the foams, and a device for testing the toxicity of various substances to which cells in or on the foams are exposed.

DETAILED DESCRIPTION OF THE INVENTION

The features and other details of the method and composition of the invention will now be more particularly described and pointed out in the claims. It will be understood that the particular embodiments of the invention are shown by way of illustration and not as limitations of the invention. The principal features of this invention can be employed in various embodiments without departing from the scope of the invention. All parts and percentages are by weight unless otherwise specified.

A suitable biopolymer is one that can form a biocompatible foam or sponge-like structure. The biopolymer is non-toxic and bioabsorbable. Further, the product of degradation of the biopolymer is non-toxic. These biopolymer include collagen, algenic acid, polyvinyl alcohol, proteins, such as laminin, fibronectin or fibrinogen activated with thrombinto form fibrin. A preferred source material for a biopolymer consists of collagen and, in particular, the skins from near-term, domestic porcine fetuses which are harvested intact, enclosed in their amniotic membranes. Collagen can be derived from other suitable animal source, such as porcine, bovine, ovine or marine animals and from many tissues, such as dermis, tendons, dental and connective tissue, as well as others. Embryonic and fetal tissues are advantageous because they include various molecular factors which are present in normal tissue at different stages of animal development. A mix of biopolymers can be used. In one embodiment, the biopolymers are collagen and fibronectin. The biopolymer can be used to create foams in the form of strips, sheets, tubes and other shapes. The shapes can be in the form of tissues or body parts to be replaced and constitute prostheses. Extracellular matrix particulates can be bonded to the biopolymers.

Extracellular matrix particulates can be taken from specific tissues. The particulates have two kinds of informational properties. The first is their molecular diversity, and the second is their microarchitecture both preserved in the preparation of the microparticulates. The preferred associations among the different molecules of the extracellular matrix are also preserved in the preparation of the microparticulates.

The extracellular matrix plays an instructive role, guiding the activity of cells which are surrounded by it or which are organized on it. Since the execution of cell programs for cell division, morphogenesis, differentiation, tissue building and regeneration depend upon signals emanating from the extracellular matrix, three-dimensional scaffolds are enriched, such as collagen sponges and foams with actual matrix constituents, which exhibit the molecular diversity and the microarchitecture of a generic extracellular matrix, and of extracellular matrices from specific tissues.

The extracellular matrix particulates can have cytokines, including growth factors necessary for tissue development. These biomolecular factors are present in normal tissue at different stages of tissue development, marked by cell division, morphogenesis and differentiation. Among these factors are stimulatory molecules that provide the signals needed for in vivo tissue repair. These cytokines including growth factors, being part of the extracellular matrix microparticulates, can stimulate conversion of an implant into a functional substitute for the tissue being replaced. This conversion can occur by mobilizing tissue cells from contiguous like tissues, from the circulation and from stem cell reservoirs; it can promote cell division, morphogenesis and differentiation. Cells can attach to the prostheses which are bioabsorbable and can remodel them into replacement tissues.

Growth factors necessary for cell growth are attached to structural elements of the extracellular matrix. The structural elements include proteins, glycoproteins, proteoglycans and glycosaminoglycans. The growth factors, originally produced and secreted by cells, bind to the extracellular matrix and regulate cell behavior in a number of ways. These factors include, but are not limited to, epidermal growth factor, fibroblast growth factor (basic and acidic), insulin growth factor, nerve growth-factor, mast cell-stimulating factor, platelet-derived growth factor, the family of transforming growth factor-β, platelet-derived growth factor, scatter factor, hepatocyte growth factor and Schwann cell growth factor. Adams et al., "Regulation of Development and Differentiation by the Extracellular Matrix" Development Vol. 117, p. 1183-1198 (1993) (hereinafter "Adams et al.") and Kreis et al. editors of the book entitled "Guidebook to the Extracellular Matrix and Adhesion Proteins," Oxford University Press (1993) (hereinafter "Kreis et al.") provide contributions which summarize extracellular matrix components that regulate differentiation and development and describe the regulatory mechanisms involved and that growth factors and extracellular matrix molecules interact in a number of ways to regulate cell behavior. Further, Adams et al. disclose examples of association of growth factors with extracellular matrix proteins and that the extracellular matrix is an important part of the micro-environment and, in collaboration with growth factors, plays a central role in regulating differentiation and development. The teachings of Adams et al. and Kreis et al. are incorporated herein by reference.

The method for forming extracellular matrix particulates for producing graft tissue includes freezing a tissue source having living cells, whereby the living cells are disrupted to form cell remnants. The tissue source is then cryomilled to produce particulates which are thawed and are processed leaving extracellular matrix particulates including cytokines. The term cytokines includes but is not limited to growth factors, interleukins, interferons and colony stimulating factors. The process of washing removes the cell remnants without removing growth and other factors necessary for cell growth, morphogenesis and differentiation. The extracellular matrix is freeze-dried and, if desired, further fragmented.

A method for forming extracellular matrix particulates for producing graft tissue is disclosed in U.S. patent application Ser. No. 07/926,885, filed Aug. 7, 1992, now abandoned, entitled "A Method for Producing Graft Tissue Extracellular Matrix". The teachings of U.S. patent application Ser. No. 07/926,885 are herein incorporated by reference. The method for forming extracellular matrix particulates for producing graft tissue includes freezing a connective tissue source having living cells, whereby the living cells are disrupted to form cell remnants. The connective tissue source is processed to remove the cell remnants without removing growth factors necessary for cell growth, differentiation, and morphogenesis to form an extracellular matrix. The extracellular matrix is freeze-dried and fragmented. The extracellular matrix is further processed to remove cytoplasmic and nuclear components without removing the growth factors necessary for cell growth to form extracellular matrix particulates. In one embodiment, the extracellular matrix particulates associated with collagen fibers in a three-dimensional matrix are exposed to cultivated cells under such conditions that the cultivated cells adhere to the extracellular matrix particulates, alone or to the particulates and the collagen fibers, thereby producing graft tissue.

A coating process can precede or accompany the application of extracellular matrix particulates to the collagen foam in order to further provide cellular and molecular binding sites on the surfaces of the collagen foams such binding sites having been compromised as a result of crosslinking. In addition, artificial microstructures, typically having a size in the range of between about 50 and 500 micrometers, composed of a matrix polymer, such as collagen, combined with other proteins, proteoglycans, glycoseaminoglycans, ECM enzymes, cytokines (including growth factors), and glycosides can be created in the form of wet or dry particulates that can be applied with the coating solution to the surfaces of the collagen foam. The selected components can be chemically or electrostatically bound to the biopolymer or can be contained in the microparticulate lattice or in some dehydrated form of the lattice.

In a preferred method for extracting the collagen from tissue, a collagen source includes porcine fetuses. The fetuses are frozen in utero with the uteri maintained in an unbroken condition with the ends tied off by string. Twelve to twenty-four hours before dissection, a uterus is removed from the freezer and placed in a 4° C. cold room. The uterus, which should still be about 90% frozen, is transferred into a large sterile dishpan. As soon as possible, the folded uterus is gently straightened. The exterior surface of the uterus is washed twice for ten minutes in 1% bleach in Milli-Q™ water and is then washed twice with sterile Milli-Q™ water to sterilize the uterus.

Under clean-room conditions using sterile, large tissue grip forceps and large scissors, and wearing sterile gloves, mask, hood and gown, the entire length of the uterus on the surface opposite the major blood vessels is opened. Care is taken not to touch or damage the amniotic membranes of the fetus. Instruments that come in contact with the outer surface of the uterus are washed with 70% ethyl alcohol and sterilized with a Bunsen burner. Each fetus is gently lifted from the uterus and the umbilicus is cut at least two centimeters from the fetus. The still mainly frozen fetus is placed into a stainless steel pan.

With sterile gloves, the amniotic membrane is removed, and the fetus is transferred to a sterile glass dish. With a sterile scalpel, such as a #11 blade, the skin around each foot is sliced to make a circular incision. A single incision is made through the skin from the first cut, along the inner surface of each limb to the midline of the ventral surface of the trunk. A midline incision is made along the ventral surface of the trunk from the tail to the neck, taking care not to penetrate the underlying muscle tissue. A skin deep circular incision is made around the circumference of the head. The body skin is peeled off. The peeled skin is placed into a sterile container (one liter centrifuge bottle with cap) on ice.

The skins are combined with an equal volume of sterile ice, and the ground tissue is washed twice in twenty liters of ice cold 0.33×phosphate buffered saline (PBS):Mill-Q™ water (1:2) with about thirty minutes allowed for tissue to settle between washes. The tissue is evenly divided into one-liter centrifuge bottles as required and each filled with 0.5M acetic acid and 4 mM EDTA. The centrifuge bottles are placed on a roller bottle apparatus for about seven days at a temperature of about 4° C.

On the eighth day after the beginning of the skin preparation, the centrifuge bottles are spun for thirty minutes at 5,000 rpm. The supernatant is aseptically collected in a sterile carboy (20 or 50 liters). The collected supernatant is filtered through four layers of sterile cheese cloth. Sterile sodium chloride is added to bring the solution to about 0.9M. It is stirred over a period of about one hour and is then placed in a cold room at about 4° C. overnight. The collagen is resuspended. The entire salt precipitated solution and the precipitate is dispensed into sterile one-liter centrifuge bottles. The bottles are centrifuged at 5,000 rpm for about thirty minutes using a 6×one-liter rotor at about 7,280 gs. The supernatant is removed, and the pellet is kept. To the pellet in each centrifuge bottle, 0.5M acetic acid having a pH of 2.5 plus 4 mM EDTA is added. The pellets are dispersed in the medium and shaken in a gyrator shaker for about sixteen hours at a temperature of about 4° C. The pellets from the bottles are transferred to a six liter flask, by rinsing each bottle with the 0.5M acetic acid, EDTA solution and pouring the mix into the flask. In the six liter flask, the pellets are dispersed with a sterile glass rod. The flask is placed on a shaker for twenty-four hours at a temperature of about 4° C. The flask is checked for degree of solubilization and resuspension. More 0.5M acetic acid and EDTA solution may be added to bring the volume to five liters.

Sterile sodium chloride is added to the flask to bring the solution to about 0.7M. It is stirred periodically over a period of one hour and then placed in a cold room at a temperature of about 4° C. overnight allowing the salt to precipitate.

The contents are shaken and dispensed into one-liter sterile centrifuge bottles and spun at about 5,000 rpm for 30 minutes at 7,280 gs. A second resuspension is conducted with the step similar to the steps described above for the first resuspension. Instead, of resuspending in six liters, a total volume of two liters is employed in the resuspension process. The flask is shaken in the cold room overnight and its volume adjusted as necessary.

The solution is dialyzed three times for about 20–24 hours against one hundred liters of ice cold 0.05% 0.5M acetic acid in the cold room (4° C.) using 6,000–8,000 MW cutoff, Spectrapore dialysis bags. The dialysis bag is slit with a sterile scalpel blade and the contents transferred into sterile 250 ml centrifuge bottles. The bottles are centrifuged at a temperature of about 4° C. at 10,000 rpm (13,000 g) for one hour. The supernatant is collected and stored in a sterile, sealed bottle.

A 0.5 ml aliquot of the supernatant is removed, combined with equal volume of concentrated hydrogen chloride and the collagen concentration measured using an hydroxyproline assay. The collagen is concentrated to a theoretical concentration of 5 mg/ml using a hollow fiber filter. The concentration can be confirmed with a hydroxyproline assay.

A solution of biopolymer prepared by the above procedure is introduced into a well. Before introduction into the well, the collagen solution is degassed under vacuum until no further bubbling is observed. In one embodiment, the solution is exposed to 5–10 mm Hg for about 30 minutes. The well is filled with an amount of polymer determined by the thickness of the foam product required. A well of about 1.2 cm diameter is filled with 4.0 microliters of solution to provide a foam of about 1.5 mm in thickness. The well can be of any size and shape to produce the required geometry of freeze-dried product. The concentration of the biopolymer in each well can be in the range of between 0.3 mg/ml of collagen to about 10 mg/ml depending on the density of product required. In a preferred embodiment, a solution having a concentration of about 3.0 mg/ml is used. While the collagen solution can be freeze-dried directly from the liquid state, in a preferred embodiment, the collagen solution is polymerized by exposure to an ammonium hydroxide vapor from a 29% solution, or by the addition of a base to the solution to form a pH of seven while forming-a gel. The rate of polymerization is proportional to temperature and can be controlled by regulating the temperature of the collagen solution in the well.

After polymerization of the solution and formation of a collagen lattice, the lattice is crosslinked by ultraviolet radiation at a wavelength of about 254 nm either before or after freeze-drying. If crosslinked before freeze-drying, the intensity of irradiation can be about $0.38 \times 10^7$ microjoules/$cm^2$. If crosslinked after freeze-drying, the intensity can be about four times the foregoing value. Exposure to ultraviolet radiation can be increased depending on the degree of crosslinking desired. Chemical crosslinking with 15 millimolar carbodiamide in 0.5×PBS can also be used.

The freeze-drying routine used to form a foam consists of a freezing, evacuation, heating cycle, which is varied as a function of polymer concentration since the eutectic temperature, that is the minimum freezing point for the entire volume of material being frozen will vary with the concentration of biopolymer in solution or in the polymerized lattice. In one embodiment, a cycle for shelf freeze-drying the collagen to form foams consists of having a temperature of about −30° C. for about 12 hours, then raising the temperature to about −26° C. and holding it for about 12 hours, then applying a vacuum of about 0.01–01 mbar for the remainder of the cycle while raising the temperature to a range of between about −10° C. and −15° C. and holding it for 8 hours and then further raising the temperature to about +20° C. and holding it for 8 hours.

If the product is crosslinked in the gel state, the foam is ready for the step of processing after it is freeze-dried. If it has not, the foam is crosslinked after it is prepared. The freeze-dried, crosslinked foam need not be removed from its casting well which is next filled with one of the following: 1) a solution of uncrosslinked collagen having a concentration in the range of between about 0.3 and 10 mg/ml, for a well having a diameter of about 1.2 cm, the volume of the added solution would be about 0.4 ml; 2) The same as (1) above but with the addition of extracellular matrix particulates mixed into the collagen solution; 3) the same as (1) above with any of the following extracellular matrix constituents alone, or in combination include but are not limited to proteins, glycoproteins, proteoglycans, extracellular matrix enzymes, cytokines, including growth factors, interleukins, interferons, colony stimulating factors, and glycosides; 4) the same as (1) above but with microparticulates of collagen or other biopolymer or hydrogel, in hydrated or dehydrated form, into which the extracellular matrix constituents have been introduced without binding, the microparticulate structures in the form of spheres can measure between about 50 and 500 μm in diameter; and 5) chemically or electrostatically binding the polymer substance to the microparticulate.

After the well is filled with the one of the above solutions, the eutectic temperature required for each type of solution is selected and a second freeze-dry cycle is carried out, but this time the product is not crosslinked so that the biological activity of the collagen coating and of any other constituents incorporated into the collagen solution remain unaffected by the processing.

Foam discs of the unfinished or finished dimensions cited above, i.e., 1.0–1.2 cm in diameter and 1.0–5.0 mm or greater in thickness can be inserted into transwells of the Corning Costar type used for carrying out cell cultures. The foam inserts, inserted into transwell containers can be of any of the four types described above: that is uncoated with collagen solution, coated with collagen solution or coated with collagen solution containing extracellular matrix components in any of the forms described above. Each foam disc is seeded with tissue cells in a tissue culture medium. The types of cells chosen to occupy the interstices of the foam, which is an open cell foam, are normally surrounded by extracellular matrix. In one embodiment, the tissue cells are mixed in a solution of neutralized collagen so that the cells become surrounded by a collagen gel in the foam. In this embodiment, cells of other phenotypes, in particular endothelial, epithelial or mesothelial can be plated on the under surface of the gel or on the upper surface of the gel, thereby constituting tissue equivalents of two, or three or more cell types.

Foam sheets, tubes, rods, cups and other shapes in the form of prostheses treated as described above with the various types of collagen solutions containing extracellular matrix components will be used as human replacement parts. For example, a 1.0 cm² rectangle having a thickness in the range of between one and three millimeters provided with a crosslinked collagen apron string can serve as a periodontal prosthesis. In this instance, all the surfaces of the foam are decorated with extracellular matrix particulates from tissues which make up teeth and those which surround teeth. The particulates are tested for selected extracellular matrix components and are shown to contain bFGF, TGF-B2, PDGF, IL1α, decorin and collagen types I and III. The periodontal prosthesis is installed as a remedial bioabsorbable device in individuals suffering from periodontal disease after preparing a tooth under treatment in a way familiar to those practiced in the art. This matrix can induce regeneration of periodontal ligaments which hold the tooth to alveolar bone, connective tissues which surround the alveolar bone and the alveolar bone itself. The foams are recognized by tissue cells because of their composition, because cells receive signals from them, are able to attache to them and remodel them. Because of their content of FGF the foams are angiogenic and capable of attracting a capillary circulation. For each of the prostheses developed tissue specific, or generic extracellular matrix constituents will be used to provide information required for tissue building and regeneration.

Foams, designed as prostheses and carrying components of the extracellular matrix, can be seeded with tissue cells prior to grafting. For example a vascular prosthesis in the form of a tube can be seeded internally with smooth muscle cells delivered in a neutralized collagen solution that gels after delivery, externally with advential fibroblasts and on its luminal surface with endothelial cells. Similarly, particulate decorated foams can be seeded with glandular cells such as those of the endocrine pancreas as means of promoting cell proliferation before and/or after implantation with the expectation that after implantation and vascularization of the cell-laden foam implant, a functional replacement glad will develop.

Equivalents

Those skilled in the art will recognize, or be able to ascertain using no more than routine experimentation, many equivalents to specific embodiments of the invention described specifically herein. Such equivalents are intended to be encompassed in the scope of the following claims.

We claim:

1. A sponge, comprising:
   a biopolymer foam comprising a biopolymer matrix having interstices surrounded by biocompatible biopolymer; and
   extracellular matrix particulates.

2. The sponge of claim 1, wherein the biopolymer is selected from the group consisting of collagen, alginic acid, polyvinyl alcohol, laminin, fibrinogen, and fibronectin.

3. The sponge of claim 1, wherein the biopolymer comprises a mixture of at least two different biopolymers.

4. The sponge of claim 2, wherein the biopolymer is collagen.

5. The sponge of claim 4, wherein the collagen is porcine collagen.

6. The sponge of claim 5, wherein the collagen is fetal porcine collagen.

7. The sponge of claim 4, wherein the collagen includes crosslinked collagen.

8. The sponge of claim 4, wherein the collagen includes uncrosslinked collagen.

9. The sponge of claim 1, wherein the extracellular matrix particulates are dispersed throughout the foam.

10. The sponge of claim 9, wherein the extracellular matrix particulates are dispersed in a biopolymer solution filling the foam.

11. The sponge of claim 1, wherein a suspension of extracellular matrix particulates in a collagen solution is coated on the surface of the biopolymer foam.

12. The sponge of claim 11, wherein the biopolymer foam and suspension are freeze-dried.

13. A vascular prosthesis comprising the sponge of claim 1 in the form of a tube.

14. The vascular prosthesis of claim 13, wherein the tube is seeded internally with smooth muscle cells, externally with adventitial fibroblasts, and on its luminal surface with endothelial cells.

15. A glandular implant comprising the sponge of claim 1, wherein the foam is seeded with glandular cells.

16. The glandular implant of claim 15, wherein the glandular cells are derived from the pancreas.

17. A periodontal prosthesis comprising the sponge of claim 1, wherein the biopolymer foam or the sponge is seeded with periodontal ligament cells.

18. A skin prosthesis comprising the sponge of claim 1.

19. A sponge, comprising:
    a biopolymer foam comprising a biopolymer matrix having interstices surrounded by biocompatible biopolymer wherein the interstices are occupied by cells; and
    extracellular matrix particulates.

20. The sponge of claim 1 further comprising cells occupying the interstices of the foam.

21. The sponge of claim 10, wherein the biopolymer is collagen.

22. The sponge of claim 1, wherein the biopolymer is derived from a pig.

23. The sponge of claim 22, wherein the biopolymer is derived from a fetal pig.

* * * * *